US008629304B2

(12) United States Patent
Stecker et al.

(10) Patent No.: US 8,629,304 B2
(45) Date of Patent: Jan. 14, 2014

(54) ELECTROCHEMICAL METHOD FOR PRODUCING 3-TERT-BUTYLBENZALDEHYDE DIMETHYL ACETAL

(75) Inventors: Florian Stecker, Mannheim (DE); Andreas Fischer, Heppenheim (DE); Jörg Botzem, Limburgerhof (DE); Ulrich Griesbach, Mannheim (DE); Ralf Pelzer, Fürstenberg (DE)

(73) Assignee: BASF SE (DE)

( * ) Notice: Subject to any disclaimer, the term of this patent is extended or adjusted under 35 U.S.C. 154(b) by 25 days.

(21) Appl. No.: 13/260,650

(22) PCT Filed: Mar. 22, 2010

(86) PCT No.: PCT/EP2010/053656
§ 371 (c)(1),
(2), (4) Date: Sep. 27, 2011

(87) PCT Pub. No.: WO2010/108874
PCT Pub. Date: Sep. 30, 2010

(65) Prior Publication Data
US 2012/0016162 A1      Jan. 19, 2012

(30) Foreign Application Priority Data
Mar. 27, 2009   (EP) ..................... 09156398

(51) Int. Cl.
C07C 45/42        (2006.01)
C07C 43/115       (2006.01)
C07C 43/307       (2006.01)
(52) U.S. Cl.
USPC ............ 568/426; 568/592; 568/659; 568/660
(58) Field of Classification Search
USPC ................... 568/426, 592, 659, 660
See application file for complete search history.

(56) References Cited

U.S. PATENT DOCUMENTS

| 4,318,783 A * | 3/1982 | Buhmann et al. ............. 205/349 |
| 4,539,081 A | 9/1985 | Degner et al. |
| 4,820,389 A | 4/1989 | Degner et al. |
| 5,507,922 A | 4/1996 | Hermeling et al. |
| 2005/0202967 A1 | 9/2005 | Hoefer et al. |
| 2012/0016162 A1 | 1/2012 | Stecker et al. |

FOREIGN PATENT DOCUMENTS

| DE | 199 04 900 A1 | 12/1999 |
| DE | 102004011427 A1 | 9/2005 |
| EP | 0 129 795 A2 | 1/1985 |
| EP | 0 287 954 A2 | 10/1988 |
| EP | 0 554 564 A1 | 8/1993 |
| EP | 0 638 665 A1 | 2/1995 |
| JP | 2738093 | 4/1998 |
| WO | WO-2009/059944 A1 | 5/2009 |

OTHER PUBLICATIONS

P. Loyson, S. Gouws, B. Barton, M. Ackermann, S. Afr. J. Chem 204, 57, pp. 53-56.
F. Vaudano P. Tissot, Electrochimica Acta 2001, 46, pp. 875-880.
Fileti, Gazz. Chim. Ital. 1884, 14, pp. 498-501.
F. Shirine, M.A. Zolfigol, K. Mohammadi, Phosphorus, Sulfur Silicon Relat. Elem. 2003, 178, 11, pp. 2357-2362.
P. Loysen, S. Gouws, B. Zeelie, S. Afr. J. Chem. 2002, 55, pp. 125-131.
Database Pubchem, 2007, Compound Summary.
Internal Search Report for PCT/EP2010/053656, mailed Jul. 22, 2010.
Internal Preliminary Report on Patentability for International Application PCT/EP2010/053656, dated Nov. 1, 2011.

* cited by examiner

*Primary Examiner* — Sikarl Witherspoon
(74) *Attorney, Agent, or Firm* — Novak Druce Connolly Bove + Quigg LLP

(57) ABSTRACT

The present invention relates to 3-tert-butylbenzaldehyde dimethyl acetal and to 3-tert-butylbenzyl methyl ether and to an electrochemical method for producing 3-tert-butyl-benzaldehyde dimethyl acetal and intermediates passed through in said method.

19 Claims, No Drawings

ELECTROCHEMICAL METHOD FOR PRODUCING 3-TERT-BUTYLBENZALDEHYDE DIMETHYL ACETAL

CROSS-REFERENCE TO RELATED APPLICATIONS

This application is a national stage application (under 35 U.S.C. §371) of PCT/EP2010/053656, filed Mar. 22, 2010, which claims benefit of EP 09156398.1, filed Mar. 27, 2009.

BACKGROUND OF THE INVENTION

The invention relates to 3-tert-butylbenzaldehyde dimethyl acetal and to 3-tert-butyl-benzyl methyl ether and to an electrochemical method for producing 3-tert-butyl-benzaldehyde dimethyl acetal.

It is known to produce substituted benzaldehyde dimethyl acetals directly by electro-chemical methoxylation of the corresponding toluenes. P. Loyson, S. Gouws, B. Barton, M. Ackermann, S. Afr. J. Chem 2004, 57, 53-56 describe such a method. A disadvantage of the electrochemical side-chain methoxylation of toluenes is that only toluenes substituted with electron-pushing radicals such as tert-butyl, methyl or alkoxy can be methoxylated in economically interesting, yields. Although radicals such as ethyl, isopropyl or isobutyl likewise have an electron-pushing effect, their benzylic protons can likewise be substituted by methoxy groups in a secondary reaction during the electrochemical reaction. Thus, p-cymene cannot be methoxylated smoothly to give cuminaldehyde dimethyl acetal, as described in F. Vaudano, P. Tissot, Electrochimica Acta 2001, 46, 875-880, since the isopropyl group is always also proportionately methoxylated.

Substituted benzaldehyde dimethyl acetals and the aldehydes on which these are based are important intermediates, e.g. in the synthesis of 2-methyl-3-phenylpropanal fragrances such as e.g. cyclamen aldehyde, Lysmeral® (BASF SE) or silvial.

EP 0 129 795 A2 describes a method for producing substituted benzaldehyde dialkyl acetals by electrooxidation of correspondingly substituted alkyltoluenes in which an electrolyte is used which comprises 50 to 90% by weight of a corresponding alkanol, 8.5 to 40% by weight of the alkyltoluene and 0.01 to 1.5% by weight of an acid comprising HOBS groups.

EP 0 554 564 A1 discloses a method for producing substituted benzaldehyde acetals, where the substituents of the aromatic have at least one benzylic hydrogen atom, by electrochemical oxidation of a corresponding benzyl ether in the presence of a corresponding alkanol and also in the presence of an auxiliary electrolyte, by electrolyzing in the acidic, neutral or weakly basic range.

EP 0 638 665 A1 discloses a method for producing substituted benzaldehyde dialkyl acetals by electrochemical oxidation of correspondingly substituted toluene compounds by oxidizing a substituted toluene compound in the presence of an alkanol and of an auxiliary electrolyte in an electrolysis cell and relieving the reaction solution obtained in this way outside of the electrolysis cell to a pressure which is 10 mbar to 10 bar lower than the pressure in the electrolysis cell.

It was an object of the present invention to provide an electrochemical method for producing 3-tert-benzaldehyde dimethyl acetal which is characterized by a very good product yield, by a very good product selectivity and by a high current yield and at the same time can be carried out readily on an industrial scale using inexpensive starting materials and reagents and/or auxiliaries.

BRIEF SUMMARY OF THE INVENTION

The object has been achieved through the provision of a method for producing 3-tert-butylbenzaldehyde dimethyl acetal of the formula (I)

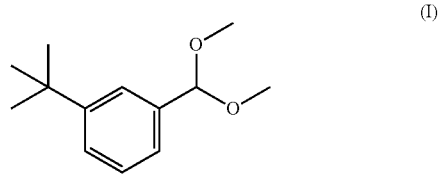

(I)

by electrochemical anodic methoxylation of 3-tert-butyltoluene of the formula (II)

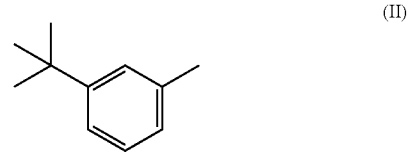

(II)

and/or 3-tert-butyl methyl benzyl compounds of the formula (III),

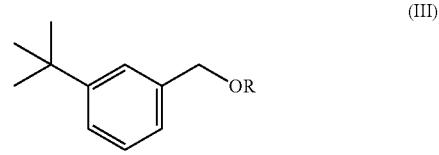

(III)

in which the radical

R is methyl or C(O)R', where R' is a straight-chain or branched alkyl radical having 1 to 6 carbon atoms, and/or di(3-tert-butylbenzyl)ether of the formula (IV)

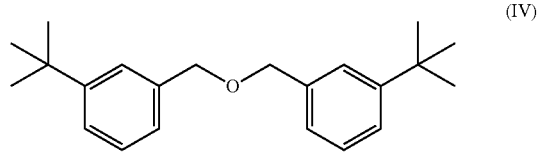 [SMILES: CC(C)(C)c1cccc(COCc2cccc(C(C)(C)C)c2)c1]

(IV)

in an electrolysis solution comprising methanol, at least one conductive salt and optionally one cosolvent or two or more different cosolvents.

The starting material used for carrying out the method according to the invention are alternatively the compounds 3-tert-butyltoluene of the formula (II)

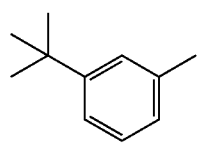

(II)

and/or the 3-tert-butyl methyl benzyl compounds of the formula (III), i.e. 3-tert-butyl methyl benzyl ethers and/or the esters of the formula (III).

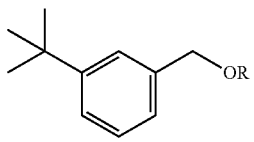

(III)

in which the radical

R is methyl or C(O)R', where R' is a straight-chain or branched alkyl radical having 1 to 6 carbon atoms, and/or di(3-tert-butylbenzyl)ether of the formula (IV)

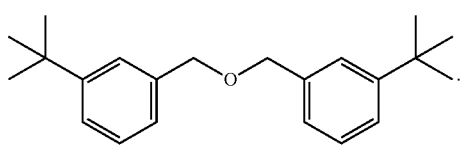

(IV)

DETAILED DESCRIPTION OF THE INVENTION

The specified compounds can in principle be used in each case in the course of the method according to the invention alone or else in the form of any mixtures of two or all three of the specified compounds.

Among the compounds of the formula (III) that can be used according to the invention, preference is given in particular to 3-tert-butyl methyl benzyl ether of the formula (IIIa)

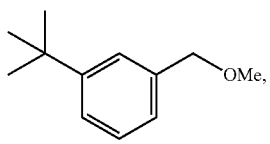

(IIIa)

in which Me is methyl. In the case of the esters of the formula (III) which can likewise be used according to the invention, the radical R' can be a straight-chain or branched alkyl radical having 1 to 6 carbon atoms, preferably methyl, ethyl, propyl or isopropyl, particularly preferably methyl. A starting compound likewise preferred according to the invention is accordingly the acetate of the formula (IIIb)

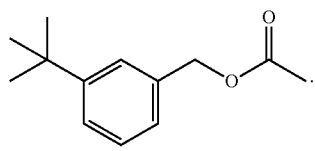

(IIIb)

Within the context of a preferred embodiment of the method according to the invention, only 3-tert-butyltoluene of the formula (II) is used as starting material. In the course of the electrochemical anodic methoxylation according to the invention, this can form firstly the specified compounds of the formulae (III), in particular 3-tert-butyl methyl benzyl ether of the formula (IIIa)

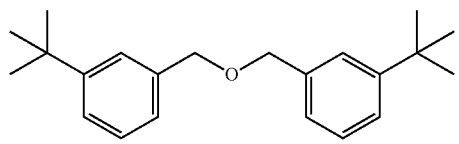

(IIIa)

in which Me is methyl, which are then for their part fully reacted or further reacted under the reaction conditions to give the desired product 3-tert-butylbenzaldehyde dimethyl acetal of the formula (I).

The 3-tert-butyltoluene of the formula (II) preferred as starting material within the context of the method according to the invention can be prepared by known methods, for example by isomerization of the para-substituted isomer, as described for example in JP 2738093.

The 3-tert-butylbenzyl methyl ether of the formula (IIIa) can be prepared for example by methoxy methylation of tert-butylbenzene with formaldehyde dimethyl acetal over a zeolite catalyst.

The production of substituted benzyl methyl ethers in general from alkylbenzenes (toluene, ethylbenzene, isobutylbenzene, cumene, tert-butylbenzene, etc.) by reaction with formaldehyde dimethyl acetal over a zeolite catalyst is described in DE 199 04 900 A1. At low conversions (<30%), good product selectivities are obtained; at higher conversions, the reaction to the diarylmethane predominates. Further options for producing the benzyl methyl ether of the formula (II) known to the person skilled in the art are the methylation of 3-tert-butylbenzyl alcohols or the reaction of 3-tert-butylbenzyl halides with methanol or methanolates in a Williamson ether synthesis.

In a further embodiment of the method according to the invention, the di(3-tert-butyl-benzyl)ether of the formula (IV)

(IV)

is used, either alone or as described above in the form of a mixture with the further possible starting materials of the formulae (II) and/or (III). Here, two equivalents of 3-tert-butylbenzaldehyde dimethyl acetal of the formula (I) are formed from one equivalent of the dibenzyl ether (IV).

The dibenzyl ether of the formula (IV) can be prepared for example by reacting the correspondingly substituted benzyl alcohol of the formula (V)

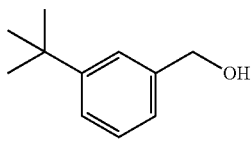

(V)

with the correspondingly substituted benzyl halide of the general formula (VI)

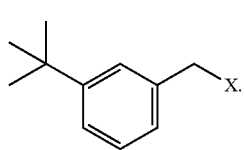

(VI)

In this connection, the method is in most cases carried out in the presence of bases for the deprotonation of the alcohols (Fileti, Gazz. Chim. Ital. 1884, 14, 498-501). The ether synthesis can also be carried out by acid-catalyzed condensation of two molecules of benzyl alcohol (Fileti, Gazz. Chim. Ital. 1882, 12, 501; F. Shirini, M. A. Zolfigol, K. Mohammadi, Phosphorus, Sulfur Silicon Relat. Elem. 2003, 178 (11), 2357-2362). There are numerous other examples of this reaction in the literature.

The di(3-tert-butylbenzyl)ether of the formula (IV) can also be produced by functionalization of unsubstituted dibenzyl ether in accordance with relevant methods which are known to the person skilled in the art, such as electrophilic aromatic substitution or Friedel-Crafts alkylation. Dibenzyl ether is an industrial product which is used, inter alia, as plasticizer.

The occurrence of alkylbenzyl methyl ethers as intermediates of the electrochemical methoxylation of alkyltoluenes, thus as intermediates of the methoxylation of p-tert-butyltoluene or p-xylene, is described in P. Loyson, S. Gouws, B. Zeelie, S. Afr. J. Chem., 2002, 55, 125-131 or P. Loyson, S. Gouws, B. Barton, M. Ackermann, S. Afr. J. Chem., 2004, 57, 53-56. The introduction of the first methoxy group here is the rate-determining step which consequently proceeds only with a moderate yield.

During the electrochemical methoxylation of the dibenzyl ether of the formula (IV), the benzaldehyde dimethyl acetal of the formula (I) is obtained directly via the dibenzyl ether bismethoxylation intermediate (VII). However, this is not stable under the reaction conditions and reacts with methanol with the release of water to give the compound of the formula (I).

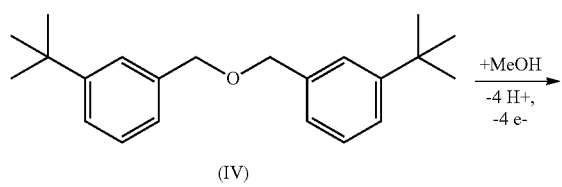

(IV)

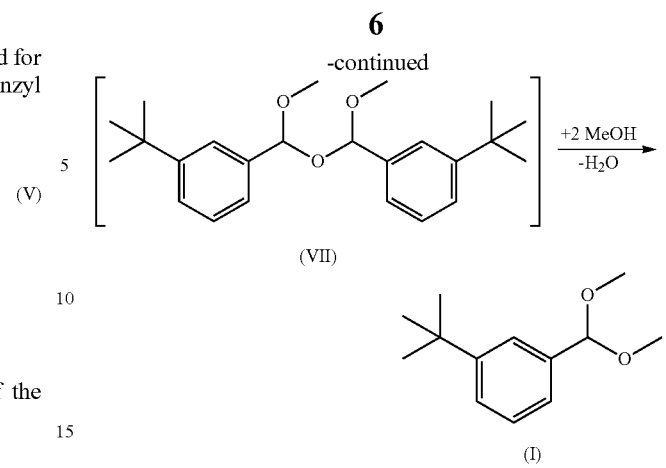

(VII)

(I)

Within the context of the method according to the invention, the electrolysis solution comprises at least methanol and at least one conductive salt as well as the selected starting materials of the formulae (II), (III) and/or (IV).

The conductive salts which may be present in the electrolysis solution are generally alkali metal, tetra($C_1$- to $C_6$-alkyl) ammonium, preferably tri($C_1$- to $C_6$-alkyl)methyl-ammonium salts. Suitable counterions are sulfate, hydrogen sulfate, alkyl sulfates, aryl sulfates, alkylsulfonates, arylsulfonates, halides, phosphates, carbonates, alkyl phosphates, alkyl carbonates, nitrate, alcoholates, tetrafluoroborate or perchlorate.

Furthermore, the acids derived from the aforementioned anions are suitable as conductive salts, thus for example sulfuric acid, sulfonic acids and also carboxylic acids.

In addition, suitable conductive salts are also ionic liquids. Suitable ionic liquids are described in "Ionic Liquids in Synthesis", edited by Peter Wasserscheid, Tom Welton, Verlag Wiley VCH, 2003, Chapters 1 to 3, and also in DE-A 102004011427.

Preferred conductive salts within the scope of the method according to the invention are methyltributylammonium methyl sulfate, methyltriethylammonium methyl sulfate, sodium methyl sulfate, sodium methanesulfonate and sulfuric acid, particularly preferably sodium methanesulfonate, methyltributylammonium methyl sulfate and methyltriethylammonium methyl sulfate, even more preferably methyltributylammonium methyl sulfate and methyltriethylammonium methyl sulfate and very particularly preferably methyltributylammonium methyl sulfate. The specified conductive salts, in particular methyltributylammonium methyl sulfate and methyltriethylammonium methyl sulfate, can be used on their own or in the form of mixtures with one another.

Within the context of a preferred embodiment of the method according to the invention, the conductive salt used is methyltributylammonium methyl sulfate and/or methyltriethylammonium methyl sulfate. Particularly preferably, the conductive salt used is methyltributylammonium methyl sulfate. Again, preference is given to using the specified conductive salts on their own or in the form of a mixture of two different conductive salts but preferably on their own.

Within the context of an advantageous embodiment of the method according to the invention, the concentration of the conductive salt in the electrolysis solution is chosen in the range from 0.1 to 20 percent by weight (% by wt), preferably in the range from 0.2 to 15% by weight, even more preferably from 0.25 to 10% by weight, even more preferably from 0.5 to 7.5% by weight and especially preferably in the range from 1 to 5% by weight.

A further preferred embodiment of the method according to the invention is one wherein the electrochemical anodic methoxylation is carried out at a temperature of the electrolysis solution in the range from 35 to 70° C., preferably in the range from 45 to 60° C.

Moreover, the method according to the invention is preferably carried out such that the electrochemical anodic methoxylation is carried out at an absolute pressure in the range from 500 to 100 000 mbar, preferably at an absolute pressure in the range from 1000 to 4000 mbar.

Customary cosolvents are optionally added to the electrolysis solution. These are the inert solvents with a high oxidation potential that are generally customary in organic chemistry. By way of example, mention may be made of dimethyl carbonate or propylene carbonate. Within the context of a preferred embodiment, the method according to the invention is therefore carried out in the presence of dimethyl carbonate and/or propylene carbonate as cosolvents.

In principle, water is also suitable as cosolvent; the fraction of water in the electrolyte is preferably less than 20% by weight.

The method according to the invention can be carried out in all customary divided or undivided electrolysis cell types. It can be carried out with good success either discontinuously or continuously. Within the context of a preferred embodiment, the method according to the invention is carried out continuously. Preference is given to working continuously with undivided flow-through cells.

Of very particular suitability are bipolar capillary gap cells or stacked plate cells in which the electrodes are configured as plates and are arranged plane parallel to one another (Ullmann's Encyclopedia of Industrial Chemistry, 1999 electronic release, Sixth Edition, VCH-Verlag Weinheim, Volume Electrochemistry, Chapter 3.5 special cell designs and Chapter 5, Organic Electrochemistry, Subchapter 5.4.3.2 Cell Design). As electrode material, precious metals such as platinum, mixed oxide electrodes such as RuOxTiOx (so-called DSA electrodes) or carbon-containing materials such as graphite, glassy carbon or diamond electrodes are preferred. Very particular preference is given to using graphite electrodes. Within the context of a preferred embodiment, the method according to the invention is carried out using a stacked plate cell.

The current densities at which the method is carried out are generally 1 to 1000 mA/cm$^2$, preferably 10 to 100 mA/cm$^2$. The method is particularly preferably carried out at current densities between 10 and 50 mA/cm$^2$. The method is generally carried out at atmospheric pressure. Higher pressures are preferably used if the method is to be carried out at elevated temperatures, in order to avoid a boiling of the starting compounds and/or of the solvent.

Suitable anode materials are, for example, precious metals such as platinum or metal oxides such as ruthenium or chromium oxide or mixed oxides of the $RuO_x$ type, $TiO_x$ and diamond electrodes. Preference is given to graphite or carbon electrodes.

Suitable cathode materials are, for example, iron, steel, stainless steel, nickel or precious metals such as platinum, and also graphite or carbon materials and also diamond electrodes. Preference is given to the system graphite as anode and cathode, and graphite as anode and nickel, stainless steel or steel as cathode.

After the reaction is complete, the electrolyte solution is worked up by general separation methods. For this, the electrolysis solution is generally firstly distilled and the individual compounds are obtained separately in the form of different fractions. Further purification can take place for example by crystallization, extraction, distillation or chromatography.

A further aspect of the present invention relates to a method for producing the 3-tert-butylbenzaldehyde of the formula (VIII)

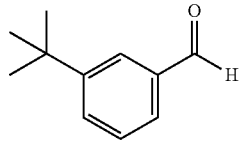

(VIII)

comprising the preparation of 3-tert-butylbenzaldehyde dimethyl acetal of the formula (I) according to the method described above and subsequent hydrolysis. The specified hydrolysis can be effected by methods known per se to the person skilled in the art, for example by simply bringing the compound of formula (I) into contact with water or an acid, such as, for example, dilute/hydrochloric acid, sulfuric acid or acetic acid.

In a further aspect, the present invention relates to 3-tert-butylbenzaldehyde dimethyl acetal of the formula (I)

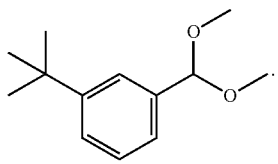

(I)

In a further aspect, the present invention relates to 3-tert-butyl methyl benzyl ether of the formula (IIIa)

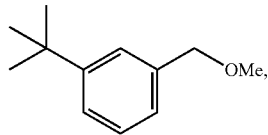

(IIIa)

in which Me is methyl.

In a further aspect, the present invention relates to di(3-tert-butylbenzyl)ether of the formula (IV)

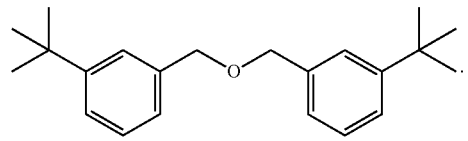

(IV)

Finally, in a further aspect, the present invention relates to the compound of the formula (VII) passed through as intermediate

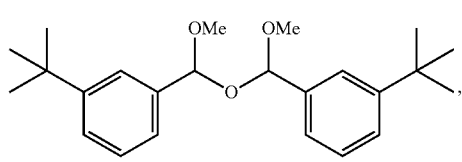

(VII)

in which Me is methyl.

The invention is illustrated in more detail by the examples below.

EXAMPLES 1 TO 5

Preparation of 3-tert-butylbenzaldehyde dimethyl acetal of the Formula (I)

Example 1

For the electrochemical methoxylation of 3-tert-butyltoluene of the formula (II), an electrolyte consisting of 105 g of the compound of the formula (II), 1.9 g of sulfuric acid (96-98%) as conductive salt and 593.1 g of methanol was electrolyzed at 45° C. and at a current density of 34 mA/cm$^2$ in an undivided capillary gap cell having 10 round graphite electrodes (A=32 cm$^2$) until an amount of charge of 15 F/mol of the compound of the formula (II) was reached. Work-up by distillation gave 33.3 g of the compound of the formula (I) and 7.5 g of 3-tert-butylbenzyl methyl ether, corresponding to a total yield of acetal and ether of 30%.

Example 2

For the electrochemical methoxylation of the compound of the formula (II), an electrolyte consisting of 140 g of the compound of the formula (II), 1.9 g of sulfuric acid (96-98%) and 3.47 g of sodium methylate (30% in methanol) as conductive salt and 554.6 g of methanol was electrolyzed at 45° C. and at a current density of 22 mA/cm$^2$ in an undivided capillary gap cell having 10 round graphite electrodes (A=32 cm$^2$) until an amount of charge of 15 F/mol of the compound of the formula (II) was reached. Work-up by distillation produced 54.5 g of the compound of the formula (I) and 17.0 g of 3-tert-butylbenzyl methyl ether, corresponding to a total yield of acetal and ether of 38%.

Example 3

For the electrochemical methoxylation of the compound of the formula (II), an electrolyte consisting of 105 g of the compound of the formula (II), 14 g of methyltributylammonium methyl sulfate (MTBS, 60% in methanol) as conductive salt and 581 g of methanol was electrolyzed at 53° C. and at a current density of 22 mA/cm$^2$ in an undivided capillary gap cell having 10 round graphite electrodes (A=32 cm$^2$) until an amount of charge of 18 F/mol of the compound of the formula (II) was reached. Work-up by distillation produced 48.3 g of the compound of the formula (I) and 10.5 g of 3-tert-butylbenzyl methyl ether, corresponding to a total yield of acetal and ether of 41%.

Example 4

For the electrochemical methoxylation of the compound of the formula (II), an electrolyte consisting of 14 g of the compound of the formula (II), 1.4 g of methyltriethylammonium methyl sulfate (MTES) as conductive salt and 54.6 g of methanol was electrolyzed at 53° C. and at a current density of 22 mA/cm$^2$ in an undivided beaker pot cell (A=10 cm$^2$) until an amount of charge of 14 F/mol of the compound of the formula (II) was reached. Work-up by distillation produced 9.99 g of the compound of the formula (I) and also 0.54 g of 3-tert-butylbenzyl methyl ether, corresponding to a total yield of acetal and ether of 54%.

Example 5

For the electrochemical methoxylation of the compound of the formula (II), an electrolyte consisting of 14 g of the compound of the formula (II), 0.42 g of sodium methanesulfonate as conductive salt and 55.6 g of methanol was electrolyzed at 53° C. and at a current density of 22 mA/cm$^2$ in an undivided beaker pot cell (A=10 cm$^2$) until an amount of charge of 19 F/mol of the compound of the formula (II) was reached. Work-up by distillation produced 8.75 g of the compound of the formula (I) and also 0.42 g of 3-tert-butylbenzyl methyl ether, corresponding to a total yield of acetal and ether of 47%.

The invention claimed is:

1. A method for producing 3-tert-butylbenzaldehyde dimethyl acetal of the formula (I),

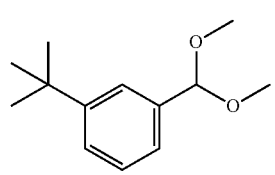

(I)

comprising electrochemical anodic methoxylating starting materials comprising 3-tert-butyltoluene of the formula (II),

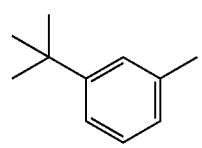

(II)

optionally 3-tert-butylbenzyl compounds of the formula (III),

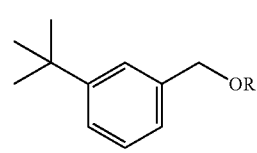

(III)

in which the radical

R is methyl or C(O)R', where R' is a straight-chain or branched alkyl radical having 1 to 6 carbon atoms, and optionally di(3-tert-butylbenzyl)ether of the formula (IV),

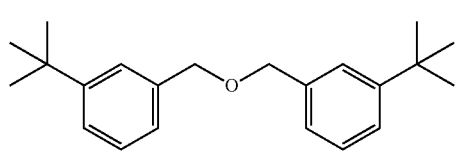

(IV)

in an electrolysis solution comprising methanol, at least one conductive salt and optionally one or more cosolvents.

2. The method according to claim 1, wherein only 3-tert-butyltoluene of the formula (II) is used as starting material.

3. The method according to claim 1, wherein the conductive salt used is methyltributylammonium methyl sulfate, methyltriethylammonium methyl sulfate, or a mixture thereof.

4. The method according to claim 1, wherein the conductive salt is methyltributylammonium methyl sulfate.

5. The method according to claim 1, wherein the cosolvent is dimethyl carbonate, propylene carbonate, or a mixture thereof.

6. The method according to claim 1, wherein the concentration of the conductive salt in the electrolysis solution is in the range from 0.1 to 20 percent by weight.

7. The method according to claim 1, wherein the electrochemical anodic methoxylation is carried out at a temperature of the electrolysis solution in the range from 35 to 70° C.

8. The method according to claim 1, wherein the electrochemical anodic methoxylation is carried out at an absolute pressure in the range from 500 to 100 000 mbar.

9. The method according to claim 1, wherein the electrochemical anodic methoxylation is carried out at a current density in the range from 10 to 100 mA/cm$^2$.

10. The method according to claim 1, wherein the electrochemical anodic methoxylation is carried out using a stacked plate cell.

11. The method according to claim 1, wherein the electrochemical anodic methoxylation is carried out continuously.

12. A method for producing 3-tert-butylbenzaldehyde of the formula (VIII)

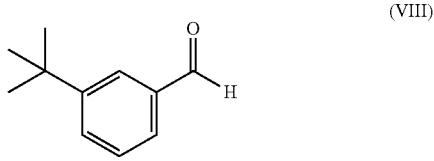
(VIII)

comprising preparing 3-tert-butylbenzaldehyde dimethyl acetal of the formula (I) according to claim 1 and subsequently hydrolyzing the 3-tert-butylbenzaldehyde dimethyl acetal of the formula (I).

13. 3-tert-Butylbenzaldehyde dimethyl acetal.

14. Di(3-tert-butylbenzyl)ether of the formula (IV)

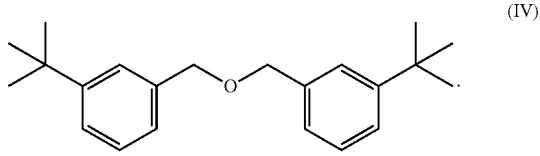 [SMILES: CC(C)(C)c1cccc(COCc2cccc(C(C)(C)C)c2)c1]
(IV)

15. A compound of the formula (VII)

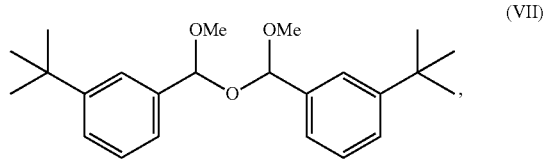
(VII)

in which Me is methyl.

16. The method according to claim 1, wherein at least one 3-tert-butylbenzyl compound of the formula (III) or di(3-tert-butylbenzyl)ether of the formula (IV) is required.

17. The method according to claim 1, wherein at least one 3-tert-butylbenzyl compound of the formula (III) is required.

18. The method according to claim 1, wherein at least one di(3-test-butylbenzyl)ether of the formula (IV) is required.

19. A method for producing 3-tert-butylbenzaldehyde dimethyl acetal of the formula (I),

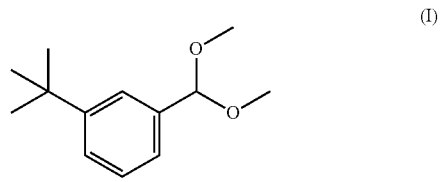
(I)

comprising electrochemical anodic methoxylating starting materials comprising 3-tert-butyltoluene of the formula (II),

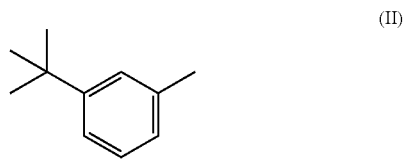
(II)

or 3-test-butylbenzyl compound of the formula (III),

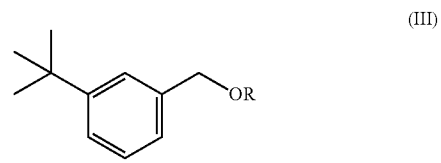
(III)

in which the radical

R is methyl or C(O)R', where R' is a straight-chain or branched alkyl radical having 1 to 6 carbon atoms, or di(3-tert-butylbenzyl)ether of the formula (IV),

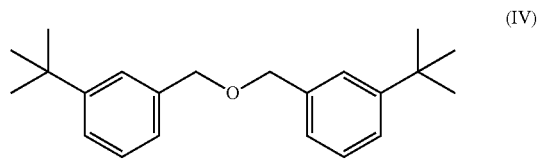 [SMILES: CC(C)(C)c1cccc(COCc2cccc(C(C)(C)C)c2)c1]
(IV)

or mixtures thereof in an electrolysis solution comprising methanol, at least one conductive salt and optionally one or more cosolvents.

* * * * *